United States Patent [19]

Nelson

[11] Patent Number: 5,360,788
[45] Date of Patent: Nov. 1, 1994

[54] PERSONAL CARE COMPOSITION CONTAINING PYRITHIONE AND A BASIC LIPOPEPTIDE

[75] Inventor: John D. Nelson, Naugatuck, Conn.

[73] Assignee: Olin Corporation, Cheshire, Conn.

[21] Appl. No.: 974,031

[22] Filed: Nov. 10, 1992

[51] Int. Cl.$^5$ .............................................. A61K 37/02
[52] U.S. Cl. ........................................ 514/9; 514/11; 514/844; 514/845; 930/10; 930/270; 930/DIG. 546
[58] Field of Search ................ 514/9, 11, 12; 530/319

[56] References Cited

U.S. PATENT DOCUMENTS

| 5,015,632 | 5/1991 | Nelson ................................... 514/55 |
| 5,120,711 | 6/1992 | Magyar et al. ........................ 514/11 |

OTHER PUBLICATIONS

Journal Article entitled "A Method for Testing for Synergy with Any Number of Agents" by M. C. Berenbaum, vol. 137, No. 2, Feb. 1978, pp. 122–130 from the Journal of Infectious Diseases.

*Primary Examiner*—F. T. Moezie
*Assistant Examiner*—David Lukton
*Attorney, Agent, or Firm*—Dale Lynn Carlson

[57] ABSTRACT

This invention relates to personal care compositions, and, more specifically, to a composition comprising a pyrithione salt or acid, a basic lipopeptide, and a suitable carrier. The pyrithione plus the lipopeptide provide antimicrobial efficacy to the personal care composition. The personal care composition is useful in a variety of dermatological items, such as soaps, shampoos, and skin care medicaments.

5 Claims, No Drawings

PERSONAL CARE COMPOSITION CONTAINING PYRITHIONE AND A BASIC LIPOPEPTIDE

FIELD OF THE INVENTION

This invention pertains generally to personal care compositions, and, more specifically, to a composition comprising a pyrithione salt or acid, a basic lipopeptide, and a suitable carrier. The pyrithione plus the lipopeptide provide antimicrobial efficacy to the personal care composition.

BACKGROUND OF THE INVENTION

Pyrithione salts, such as zinc and sodium pyrithione which are commercially available under Olin Corporation's registered trademark Omadine ®, are known to have broad antibacterial and antifungal activity. Pyrithione salts have been disclosed for use in personal care items, as illustrated by the disclosures of U.S. Pat. No. 5,015,632 describing the use of chitosan pyrithione as an antimicrobial agent in such products.

Basic lipopeptides, such as polymyxin B, colistin (also called polymyxin E), and octapeptin are known in the art. The primary use of these antibiotics is to treat superficial infections, as disclosed, for example, in U.S. Pat. No. 5,120,711. More specifically, the '711 patent discloses the use of antibiotics, such as polymyxin B, in combination with clotrimazole or chlorquinaldol in the preparation of synergistically active veterinary compositions useful for the treatment of mastitis and metritis. Unfortunately, these lipopeptides are much more expensive than might be desired for use in personal care products. Accordingly, new antimicrobial compositions that are efficaceous yet not prohibitively expensive would be highly desired by the personal care products manufacturing community.

SUMMARY OF THE INVENTION

In one aspect, the present invention relates to a personal care composition comprising a carrier and an antimicrobially effective amount of a combination of a pyrithione and a lipopeptide antibiotic. Preferably, the antimicrobial combination consists essentially of the pyrithione and the lipopeptide antibiotic.

In another aspect, the present invention relates to a method of using the above antimicrobial combination comprising incorporating the combination into a personal care composition, preferably for use as a skin care medicament.

These and other aspects will become apparent upon reading the following detailed description of the invention.

DETAILED DESCRIPTION OF THE INVENTION

It has now been surprisingly found in accordance with the present invention that a composition comprising a combination of pyrithione with a lipopeptide antibiotic provides synergistic biocidal effectiveness making the combination particularly useful in personal care compositions. As use herein, the term "synergistic antimicrobial effectiveness" means that the composition exhibits greater antimicrobial activity than the additive amounts of activity provided when each component of the combination is employed alone. The composition exhibits synergistic antimicrobial activity with respect to the growth of microorganisms, notably bacteria and fungi. The antimicrobial activity is provided during use of the combination, for example, in personal care items, such as shampoos and skin care medicaments.

The synergistic activity of the combination of polymyxin and pyrithione permit the use of substantially lower doses of each component than would otherwise be needed to provide an antimicrobially effective amount. This provides a substantial cost savings, particularly in view of the relatively high cost of polymyxin. The combination is suitably utilized as a cosmetic preservative or incorporated into ointments, coatings, or antiseptic scrubs for the treatment of bacterial and fungal skin, nail, and scalp infections, including ringworm, athlete's foot, and dandruff.

The pyrithione used in the process and composition of this invention is preferably a pyrithione salt, such as sodium pyrithione, zinc pyrithione, chitosan pyrithione, magnesium disulfide pyrithione, copper pyrithione, and the like, although pyrithione acid can be used if desired. More preferable pyrithione salts include sodium pyrithione, copper pyrithione, and zinc pyrithione, most preferably zinc pyrithione.

The lipopeptide useful in the present invention is suitably any such antibiotic, such as, for example, polymyxin B, polymyxin E (also referred to as colistin). octapeptin, combinations thereof, and the like. The preferred antibiotic is polymyxin B, which is commercially available and is preferably utilized in the present invention in the form of the sulfate salt. As used herein, the term "polymyxin B" refers to polymyxin B and to its antimicrobial derivatives such as the hydrochloride, sulfate, palmitate, methanesulfonate and oxalate salts. The anionic moieties of such salts do not substantially affect the synergistic antimicrobial activity of the compositions of the invention, and such salts can be employed advantageously therein.

The weight ratio of pyrithione to antibiotic employed in the compositions of the present invention is preferably between about 1:30 and about 700:1, more preferably between about 1:1 and about 100:1. The pyrithione and antibiotic is employed in a total amount sufficient to provide at least a microbiostatically effective concentration in the composition in which they are utilized. Preferably, the pyrithione and the antibiotic are each employed in the composition in an amount of between about 0.1 and about 1,000, more preferably between about 1 and about 1000 ppm for the pyrithione and between about 0.1 and about 100 ppm for the polymyxin.

Also present in the personal care compositions of the present invention is a suitable inert carrier, such as water, petrolatum jelly, mineral oil, lanolin, aloe, fatty acids such as steric acid, combinations thereof, and the like. The amount of carrier employed in the personal care composition can vary over a wide range of as low as 20 weight percent to as high as about 99 weight percent, preferably at least about 80 weight percent, more preferably at least about 90 weight percent, based upon the total weight of the composition depending upon the specific application envisioned.

The novel compositions of the present invention are useful as disinfectants and preservatives, in a liquid or spreadable solid form, alone or in combination with an inert carrier such as water, liquid hydrocarbons, ethanol, isopropanol, or the like. They can be employed using conventional procedures to control bacteria and fungi in various substrates, and can be applied to bacterial or fungal organisms or their substrates in an antimicrobial amount by conventional procedures such as spraying, dipping, drenching impregnation, and the like.

EXAMPLE 1

Determinations of minimum inhibitory concentrations (MIC's) of the two compounds (pyrithione salts and/or polymyxin sulfate) in a nutrient broth (alone and in mixtures) were conducted to evaluate interactions. Stock solutions of pyrithione salts and/or polymyxin sulfate were diluted in Tryptic Soy Broth (Difco), and the dilutions were inoculated with an equal volume of bacterial culture ($10^6$/ml) or fungal spore suspension ($10^5$/ml) in Tryptic Soy Broth and incubated at 28° C. for 3–7 days. The highest dilution free of growth was determined to be the MIC, as given in Table 1 below.

The interaction of the antimicrobials was determined according to an accepted procedure (M. C. Berenbaum). The concentration of each agent in the combination that inhibits the organisms is expressed as a fraction of the concentration that causes the same effect when the same agent is tested alone (i.e., its fractional inhibitory concentration, FIC). If the sum of the FIC's is 1, the combination is additive in its antimicrobial effect; if the sum is $<1$, the combination is synergistic; and if the sum is $>1$, the combination is antagonistic. According to this criterion, mixtures of sodium pyrithione and polymyxin acted in synergism against 15 of 18 bacteria and fungi, resulting in 2- to 32-fold reductions in MIC's relative to the pure compounds over a range of sodium pyrithione to Polymyxin of 1/20 to 650/1 (Table 1).

Similarly, zinc pyrithione acted in synergism with polymyxin against 12 of 18 bacteria and fungi, with 2- to 32-fold reductions in MIC's using a range of zinc pyrithione to polymyxin ratios of 1/32 to 256/1 (Table 2).

TABLE 1

| | SYNERGISM OF SODIUM PYRITHIONE (SP) POLYMYXIN B (PB) MIXTURES | | | | | |
|---|---|---|---|---|---|---|
| | Minimum Inhibitory Concentration (ppm)[a] | | | | | Sum of Fractional |
| | Compound Used Alone | | Mixture | | SP[c] | Inhibitory |
| Organism[b] | SP | PB | SP | PB | PB | Concentrations[d] |
| BACTERIA: | | | | | | |
| Pseudomonas Stutzeri | 81.3 | 0.3 | 40.6 | 0.1 | 325–650 | 0.75 |
| Pseudomonas fluorescens | 135.5 | 10.7 | 6.7 | 1.2 | 3–10 | .16 |
| Citrobacteria frenndii | 12.7 | 0.5 | 6.7 | 0.1 | 41–81 | 0.75 |
| Pseudomonas oleovorans | 12.7 | 0.3 | 3.2 | $<0.1$ | 41–163 | 0.50 |
| Pseudomonas rubescens | 23.7 | $<0.1$ | 2.5 | $<0.1$ | 650 | 0.52 |
| Alcaligens faecalis | 30.5 | 1.4 | 9.3 | 0.5 | 5–41 | 0.87 |
| Pseudomonas aeruginosa | 162.6 | 0.7 | 81.3 | 0.3 | 163–325 | 1.08 |
| Proteus mirabilis | 325.1 | $>2048.0$ | 61.0 | 288.0 | 1/20–1 | $<0.33$ |
| FUNGI: | | | | | | |
| Candida albicans | 33.9 | 256.0 | 6.7 | 64.0 | 1/20–1/10 | 0.46 |
| Trichophyton mentagrophytes | 20.3 | 32.0 | 8.5 | 26.7 | 1/10–1/3 | 1.25 |
| Aspergillus niger | 121.9 | 1536.0 | 40.6 | 256.0 | 1/10 | 0.57 |
| Penicillin pinophilium | 20.3 | 256.0 | 5.1 | 48.0 | 1/20–1/10 | 0.44 |
| Aureobasidium pullulans | 15.2 | 256.0 | 5.1 | 48.0 | 1/20–1/10 | 0.57 |
| Gliocladium virens | 108.3 | 74.7 | 15.2 | 21.3 | 1/10–1 | 0.51 |
| Chaetomium globosium | 12.7 | 24.0 | 3.8 | 16.0 | 1/10–1/5 | 1.13 |
| Fusarium solani | 243.8 | 128.0 | 40.6 | 32.0 | 1 | 0.44 |
| Fusarium sp. | 243.8 | 128.0 | 40.6 | 32.0 | 1 | 0.44 |
| Cephalosporium sp. | 50.8 | 256.0 | 15.2 | 12.0 | 1 | 0.42 |

[a]Compounds were serially diluted in Tryptic soy Broth (DIFCO), inoculated and incubated at 28° C. Average of two to four determinations. Active ingredients basis. PB 7610 units/mg.

[b]Each dilution contained $10^6$ bacteria/ml of $10^5$ fungi/ml. Bacteria were incubated 3 days and fungi were incubated 6–7 days.

[c]Ratio of Sodium pyrithione to Polymyxin B sulfate in mixture

[d]Criterion of synergism according to Berenbaum (1). Mixture is synergistic if sum $<1$ (avg. of two to four determinations).

TABLE 2

SYNERGISM OF ZINC PYRITHIONE (ZP) POLYMYXIN B (PB) MIXTURES

| Organism[b] | Minimum Inhibitory Concentration (ppm)[a] | | | | ZP[c] PB | Sum of Fractional Inhibitory Concentrations[d] |
|---|---|---|---|---|---|---|
| | Compound Used Alone | | Mixture | | | |
| | SP | PB | SP | PB | | |
| BACTERIA: | | | | | | |
| Pseudomonas Stutzeri | 4.0 | 0.3 | 4.0 | <0.1 | 16–128 | 1.04 |
| Pseudomonas fluorescens | 106.7 | 6.7 | 4.7 | 0.4 | 0.11 | 0.16 |
| Citrobacteria freundii | 8.0 | 0.4 | 3.3 | 0.1 | 16–64 | 0.71 |
| Pseudomonas oleovorans | 6.7 | 0.5 | 4.0 | 0.2 | 16–32 | 1.00 |
| Pseudomonas rubescens | 3.3 | <0.1 | 3.3 | <0.1 | 256 | 1.42 |
| Alcaligens faecalis | 10.7 | 3.3 | 6.7 | 0.6 | 8–32 | 0.85 |
| Pseudomonas aeruginosa | 288.0 | 1.0 | 112.0 | 0.5 | 128–256 | 1.19 |
| Proteus mirabilis | 4.0 | >2048.0 | 2.0 | 64.0 | 1/32 | <0.53 |
| FUNGI: | | | | | | |
| Candida albicans | 8.0 | 341.3 | 4.0 | 74.7 | 1/32–1/8 | 0.75 |
| Trichophyton mentagrophytes | 8.0 | 53.0 | 8.0 | 26.7 | 1/4–1/2 | 1.58 |
| Aspergillus niger | 32.0 | 1024.0 | 16.0 | 298.7 | 1/32–1/8 | 0.79 |
| Penicillin pinophilium | 16.0 | 128.0 | 4.0 | 32.0 | 1/8 | 0.50 |
| Aureobasidium pullulans | 8.0 | 288.0 | 4.0 | 80.0 | 1/32–1/16 | 0.84 |
| Gliocladium virens | 80.0 | 64.0 | 24.0 | 20.0 | 1–2 | 0.69 |
| Chaetomium globosium | 6.7 | 26.7 | 2.7 | 13.3 | 1/8–1/4 | 1.00 |
| Fusarium solani | 64.0 | 85.3 | 13.3 | 37.3 | 1/8–1 | 0.75 |
| Fusarium sp. | 64.0 | 106.7 | 18.7 | 42.7 | 1/8–1 | 0.79 |
| Cephalosporium sp. | 16.0 | 170.7 | 4.0 | 42.7 | 1/16–1/8 | 0.54 |

[a]Stock solutions of ZP in dimethylsulfoxide and PB in sterile water were serially diluted in Tryptic soy Broth (DIFCO), inoculated and incubated at 28° C. Average of two to four determinations. Active ingredients basis. PB 7730 units/mg.
[b]Each dilution contained $10^6$ bacteria/ml or $10^5$ fungi/ml. Bacteria were incubated 6 days, and fungi were incubated 7 days.
[c]Ratio of ZP to PB sulfate in mixture.
[d]Criterion of synergism according to Berenbaum (1). Mixture is synergistic if sum <1. (Avg. of two to four determinations).

Mixtures of pyrithiones and polymyxin may be employed as a medicament when incorporated into a suitable skin cream formulation. A typical mixture consists of 2.2% hydroxylated lanolin, 16.3% lanolin alcohol, 21.7% mineral oil, 16.3% microcrystaline wax (170°–175° F. m.p.), and 43.5% water. Mixtures of pyrithiones and polymyxin are added to the water phase (1 to 1000 ppm) which is heated to 65° C. and added with mixing to a 65° C. mixture of the remaining ingredients. The resulting mixture is cooled to 35° C. with mixing, homogenized, and packed.

While the invention has been described above with references to specific embodiments thereof, it is apparent that many changes, modifications and variations in the materials, arrangements of parts and steps can be made without departing from the inventive concept disclosed herein. Accordingly, the spirit and broad scope of the appended claims is intended to embrace all such changes, modifications and variations that may occur to one of skill in the art upon a reading of the disclosure. All patent applications, patents and other publications cited herein are incorporated by reference in their entirety.

Having thus described the invention, what is claimed is:

1. A personal care composition comprising a carrier and an antimicrobially effective amount of a combination of sodium pyrithione and polymyxin B sulfate antibiotic wherein said sodium pyrithione and said polymyxin B sulfate are employed in said composition in a weight ratio of sodium pyrithione to polymyxin B sulfate of between 0.05 and 650.

2. A personal care composition comprising a carrier and an antimicrobially effective amount of a combination of zinc pyrithione and polymixin B sulfate antibiotic wherein said zinc pyrithione and said polymixin B sulfate are employed in said composition in a weight ratio of zinc pyrithione to polymixin B sulfate of between 0.03 and 256.

3. The composition of claims 1 or 2 wherein said combination consists essentially of said pyrithione and said antibiotic.

4. The composition of claims 1 or 2 wherein said pyrithione and said antibiotic are employed in said composition in a weight ratio of pyrithione to antibiotic of between about 1:1 and about 100:1.

5. The composition of claims 1 or 2 wherein said carrier is an inert carrier selected from the group consisting of water, petrolatum jelly, mineral oil, lanolin, aloe, fatty acids, and combinations thereof.

* * * * *

UNITED STATES PATENT AND TRADEMARK OFFICE
CERTIFICATE OF CORRECTION

PATENT NO. : 5,360,788
DATED : November 1, 1994
INVENTOR(S) : John D. Nelson, Jr.

Page 1 of 2

It is certified that error appears in the above-indentified patent and that said Letters Patent is hereby corrected as shown below:

At column 1, line 61 after "As" delete "use", and insert --used-- in its place.

In Table 1 and 2, column 1, line 2, delete "Stutzeri" and insert --stutzeri-- in its place.

In Table 1 and 2, column 1, line 5, delete "Citrobacteria" and insert --Citrobacter-- in its place.

In Table 1 and 2, column 1, line 6, delete "frenndii" and insert --freundii-- in its place.

In Table 1 and 2, column 1, line 11, delete "Alcaligens" and insert --Alcaligenes-- in its place.

In Table 1 and 2, column 1, line 25, delete "pinophilium" and insert --pinophilum-- in its place.

UNITED STATES PATENT AND TRADEMARK OFFICE
CERTIFICATE OF CORRECTION

PATENT NO. : 5,360,788
DATED : November 1, 1994
INVENTOR(S) : John D. Nelson, Jr.

It is certified that error appears in the above-indentified patent and that said Letters Patent is hereby corrected as shown below:

In Table 1 and 2, column 1, line 31, delete "globosium" and insert --globosum-- in its place.

In Table 1 and 2, at footnote d, after "Berenbaum" delete (1).

In the heading of Table 2 at line 6, columns 2 and 4, please delete "SP" in both instances and insert --ZP-- in its place.

Signed and Sealed this

Twenty-first Day of February, 1995

*Attest:*

BRUCE LEHMAN

*Attesting Officer*     *Commissioner of Patents and Trademarks*